United States Patent [19]

Greenberg

[11] Patent Number: 4,573,452

[45] Date of Patent: Mar. 4, 1986

[54] SURGICAL HOLDER FOR A LAPAROSCOPE OR THE LIKE

[76] Inventor: I. Melvin Greenberg, 62 The Hemlocks, Roslyn Heights, N.Y. 11576

[21] Appl. No.: 630,372

[22] Filed: Jul. 12, 1984

[51] Int. Cl.⁴ ............................................. A61B 17/02
[52] U.S. Cl. ......................................... 128/20; 128/6
[58] Field of Search ..................................... 128/6, 20

[56] References Cited

U.S. PATENT DOCUMENTS

| | | | |
|---|---|---|---|
| D. 239,131 | 3/1976 | Adler | D54/13 A |
| 3,858,578 | 1/1975 | Milo | 128/20 |
| 4,099,521 | 7/1978 | Nestor et al. | 128/20 |
| 4,143,652 | 3/1979 | Meier et al. | 128/20 |
| 4,254,763 | 3/1981 | McCready et al. | 128/20 |
| 4,461,284 | 7/1984 | Fackler | 128/20 |

Primary Examiner—William H. Grieb
Attorney, Agent, or Firm—Bauer & Amer

[57] ABSTRACT

Mechanical components for holding and positioning a laparoscope incident to its use during surgery, wherein a selectively tensionable cable-type component is released for moving the laparoscope almost into its desired position and then tensioned into a rigid structure, and then a ball and socket joint is rendered operational to complete the moving of the laparoscope, if need be, to precisely position this instrument in its required anatomy-viewing position.

4 Claims, 4 Drawing Figures

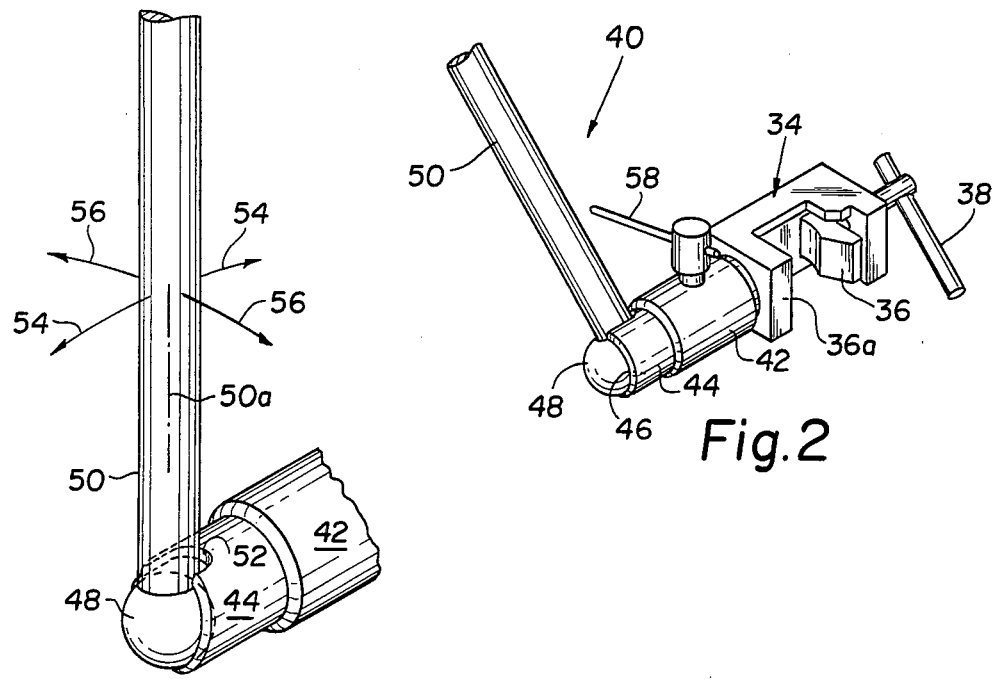
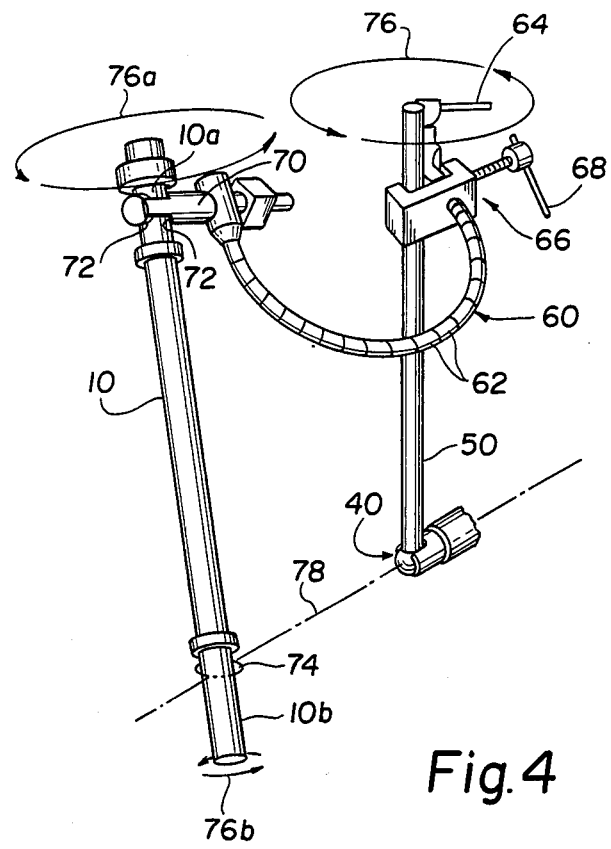
Fig. 2
Fig. 3
Fig. 4

SURGICAL HOLDER FOR A LAPAROSCOPE OR THE LIKE

The present invention relates generally to surgical support structure for a laparoscope, and more particularly to a unique combination of rigid and flexible components which provide the capability of precisely positioning the laparoscope incident to its use during surgery, but while maintaining, once said position is established, a necessary rigidity to avoid inadvertent slippage or other movement from that position.

The advantages are already well known, from such prior patents, for example, as U.S. Pat. Nos. 4,254,763 and 4,143,652, that surgical retractors, clamps and the like held by mechanical components result in a reduction in personnel and thus correspondingly in a reduction in expense, as well as providing other noteworthy benefits. Heretofore, however, the surgical instruments so held or supported did not impose critical requirements for positioning, so that they could be properly used during the surgical procedure. For example, if to allow unimpeded positioning, the support structure was comprised of a multiplicity of interconnected link elements on a flexible traction element in which such link elements, because possessing at one end a ball and at the other end a complementary ball socket, could be made to assume any shape necessary for positioning and then caused to assume a rigid mode by the tightening of said traction element, this unimpeded positioning would be at the expense of possibly not having adequate retention force to prevent slippage and other inadvertent movement from the surgical position established for the supported instrument. With a laparoscope, for example, a precise anatomy-viewing position must be established, and once established securely maintained, otherwise the viewing and internally inserted end of the laparoscope might, due to slippage, exert pressure on tissues, and especially on soft organs, such as the liver, pancreas, or intestines, and otherwise introduce a complication.

Broadly, it is an object of the present invention to provide structure for readily positioning a laparoscope prior to the use thereof, during surgery, which also is of noteworthy rigidity to obviate slippage or inadvertent movement in the laparoscope, and which otherwise overcomes the foregoing and other shortcomings of the prior art. Specifically, it is an object to provide a laparoscope-positioning component with a strategically located ball and socket joint component, so that in such combination the objectives of flexibility for positioning and of rigidity for secure weight support are uniquely balanced and readily achieved.

An improved surgical holder and positioner for a laparoscope or the like, such as an endoscope, demonstrating objects and advantages of the present invention includes an open ring and means for supporting same in a fixed horizontal orientation over a patient having an incision for the insertion of the laparoscope proximal end. A generally vertically oriented support rod is mounted adjacent its lower end at a selected location on the open ring and a selectively tensionable member extends from an end thereof engaged to the laparoscope to engagement of its opposite end to the upper end of the support rod. As a result, prior to the tensioning of the tensionable member, the laparoscope proximal end is manipulatable into a position that is proximate to that which is necessary for proper viewing of the anatomy on which the surgery is being performed. Completing the structure is a ball and socket joint that is provided at a strategic location at the lower end of the support rod for permitting the rod to be urged through conical movement with one hand by the surgeon while sighting down the laparoscope. As a consequence, the laparoscope proximal end partakes of corresponding conical movement incident to assuming a more precise anatomy-viewing position while the weight of the supporting and positioning components remains supported on the open ring.

The above brief description, as well as other objects, features and advantages of the present invention will be more fully appreciated by reference to the following detailed description of a presently preferred, but nonetheless illustrative embodiment in accordance with the present invention, when taken in conjunction with the accompanying drawings, wherein:

FIG. 2 is a partial perspective view of the ball and socket joint of the holder;

FIG. 3 is another perspective view illustrating degrees of motion of the ball and socket joint; and FIG. 4 is a perspective view illustrating the corresponding movement of the interconnecting laparoscope and rod component having the ball and socket joint.

Figure 1:
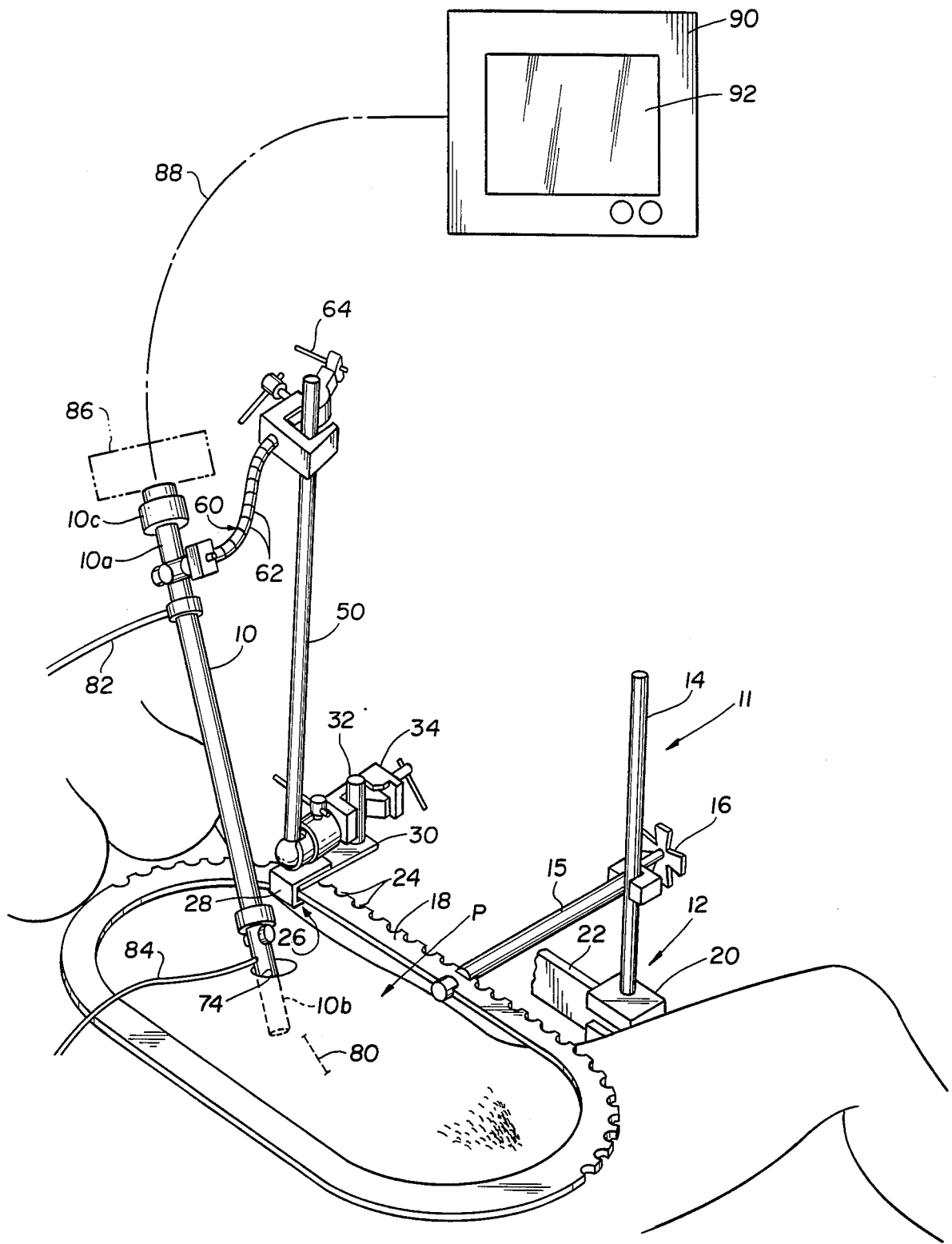
FIG. 1 is a perspective view illustrating the improved surgical holder for a laparoscope or similar instrument according to the present invention during a typical surgical procedure.

In FIG. 1 there is illustrated a typical 5 mm diagnostic laparoscope 10 as it would be held in proper viewing position during a surgical procedure, which laparoscope could, of course, also be larger or 10 mm in diameter if used for operative or instrument-inserting purposes. Included in the holding structure is a surgical ring assembly 11 for supporting the laparoscope 10 which is basically the assembly illustrated and described in U.S. Pat. No. 4,254,763, which, by this reference, is incorporated herein. More particularly, the ring assembly 11 is illustrated attached to a surgical operating room table 12 in a position as it would assume during an operation on a simulated patient P. The main components comprising this surgical ring assembly are an elongated support post 14, an elongated extension rod 15 which is connected to support post 14 by a coupling device 16, and a subtantially flat, oval-shaped ring member 18. The attachment to the surgical operating room table 12 is made by an adjustable clamp 20 attached to a rail 22 provided on each side of the table and generally extending the length thereof.

As may be readily appreciated from FIG. 2, and as is described in U.S. Pat. No. 4,254,763, the ring member 18 is substantially oval in shape and has an open center area which provides a large region for the surgical procedure. The ring member also includes a plurality of spaced indentations 24 to facilitate making a clamping connection thereto, all as will be subsequently explained. From what has been described, it should be readily appreciated that the cantilever effect of the elongated extension rod 15 and the further extension provided by the rigid member 18 allows the entire ring assembly to sufficiently reach across the patient P so that this assembly can be located only on one side of the patient, without requiring a second support arm on the other side of the patient. It is for this reason that the ring assembly 11 is selected as the most preferable in providing the support to the improved laparoscope holder of the present invention, which will now be described in detail.

At a selected location about the open ring 18, as at 26, there is provided a C-shaped clamp 28 which frictionally engages an end of a plate 30 having at its opposite end an upstanding post 32. As is perhaps best understood from FIG. 2 in conjunction with FIG. 1, adapted to be attached to the post 32 is a mounting device or vise 34 of conventional and well understood construction which includes a movable jaw 36 operated by a rotatable lever 38 so that, in practice, the post 32 is securely engaged between the movable jaw 36 and an opposing stationary jaw 36a.

As shown in FIG. 2, an integral part or connection to vise 34 is a ball and socket joint, generally designated 40, of a well understood operational mode and construction. It will also be understood that the ball and socket joint 40 hereof is readily commercially available and is similar to the ball and socket joint described and illustrated in U.S. Pat. No. 4,143,652, which, by this reference, is incorporated herein.

For present purposes, it suffices to note that the ball and socket joint 40 includes a cylindrical housing 42 in which there is rotatably disposed a sleeve 44 which seats at its outer end in a socket-shaped compartment 46 a ball 48 which is provided at the lower end of a support rod 50.

As is perhaps best shown in FIG. 3, to which figure reference should now be made, the lower end of the rod 50 operates in clearance provided by a slot 52 in the sleeve 44, so that the rod is pivotable in the opposite directions noted by the reference arrows 54. The rod 50 is also movable in the opposite directions denoted by the reference arrows 56 as a result of the rotative movement of sleeve 44 within the housing 42. As is well understood, a turning of a lever 58 of the ball and socket joint 40 is operatively effective to selectively engage or release the sleeve 44 and ball 48 with respect to the movements 54, 56. That is, the turning of lever 58 in one direction releases the sleeve 44 and ball 48, so that rod 50 can be moved in the directions 54, 56, which, as will be subsequently explained is essentially a conical movement about the vertical axis 50a of the rod 50, while rotation of the lever 58 in an opposite direction causes, in a well understood manner, frictional engagement of the sleeve 44 and ball 58 so that the rod 50 is fixed or locked in the position of movement it occupies at the time lever 58 is turned.

Reference should now be made to FIG. 4 in conjunction with FIG. 1. Completing the improved holder for the laparoscope 10 hereof is a selectively tensionable member 60 which will be understood to be readily available from numerous commerical sources and of a well understood construction composed of a multiplicity of link elements, individually and collectively designated 62, wherein each link 62 possesses at one end a ball and at the other end a complementary ball socket. The link elements 62, in turn, are threaded, in the manner of pearls upon a string of pearls, onto an internal flexible traction element (not shown). Completing the construction of the member 60 is a lever means 64 which, in a well understood manner, can effectuate the tightening of the traction element, so that the interconnected links 62, which, as already noted, are composed of a multiplicity of ball and socket joints which are arranged in a row, are caused to assume a rigid structure, i.e., a structure that can be arrested at any position selected by the surgeon or other user of the device, such as the arcuate shape of FIG. 4 or the S shape of FIG. 1. It will be understood that the selectively tensionable member 60 may be of the type described in U.S. Pat. No. 3,858,578, which patent by this reference, is incorporated herein. In practice, effective results have been achieved using a selectively tensionable or flexible member 60 as illustrated in U.S. Design Patent D 239,131.

As illustrated in the drawings, member 60 includes at one end a vise clamp 66 which, by appropriate manipulation of its lever 68 achieves attachment of the flexible member 60 to the upper end of the rod 50. At its opposite end, flexible member 60 includes a clamp 70 which preferably has padded jaws 72 which in a well understood manner are engaged to the exposed or distal end 10a of the laparoscope 10.

With specific reference to FIG. 1, it will now be explained how the improved holder and positioner for the laparoscope 10 according to the present invention, is used during a typical surgical procedure.

As the first step of the procedure it will be understood that the ring assembly 11 is set in place in overlying relation to the patient P. The rod 50 with its ball and socket joint 40 is then supported on the open ring 18 of the assembly 11, the rod 50 being in an initial vertical orientation as illustrated in FIG. 1. Assuming that the surgical procedure is general abdominal surgery, an incision 74 is made in the patient's abdomen, typically near the umbilicus, for insertion of the laparoscope proximal end 10b. It will be understood that at this time the laparoscope 10 and rod 50 are interconnected with the flexible member 60 and that the control member 64 is in its operative position releasing the individual links 62 so that member 60 is readily flexed and thus does not impede positioning movement of the laparoscope 10. The surgeon sighting down the eyepiece 10c can thus effectively manipulate the laparoscope proximal end 10b so that it is in a position very close to that which is required for proper viewing of the internal anatomy of the patient that is the object of the surgical procedure. Once this positioning is achieved for the laparoscope 10, the control lever 64 is turned to lock or fix the flexible member 60 in whatever shape it has assumed in order to allow for the positioning of the laparoscope 10. Once the member 60 has been rigidified it will be understood that it will not inadvertently move from its assumed shape, since it will be understood that the member 60 is designed to readily support four pounds. That is, it will be understood that member 60 is approximately 10 inches and that the individual links 62 which provide this length are readily fixed in relative position to each other upon the twisting of lever 64 which pulls taut the internal cable or flexible traction element such that the frictional engagement between the balls and their cooperating socket compartments will resist movement against at least four pounds of force.

Although it is possible that the laparoscope proximal end 10b will be in the precise viewing position required for the surgical procedure solely as the result of the initial manipulation by the surgeon and the position of movement achieved in the rigidified flexible member 60, the present invention contemplates that this might not always be the case and that some additional movement is necessary in positioning the laparoscope proximal end 10b. It is thus an essential contribution of the present invention to provide the ball and socket joint 40 for the lower end of the support rod 50. It should of course be appreciated that the entire weight of the laparoscope 10, interconnecting member 60, and the support rod 50 itself, are supported in the sleeve 44 of the ball and socket joint 40, which joint 40 is, in turn, supported in the fixed open ring 18. To achieve the additional degree of movement in the laparoscope proximal end 10b that may be needed for its proper anatomy-viewing positioning, the surgeon merely moves the lever 58 into its operative position releasing the support rod 50 for universal movement as previously described and illustrated in specific reference to FIG. 3. The surgeon, however, may maintain his physical contact with one hand on the lever 58 and using his other hand grasp the upper end of support rod 50 and manipulate said rod 50 through the degrees of movement 54, 56, which essentially would be a conical movement about the vertical axis 50a of the support rod 50. This conical movement is illustrated in FIG. 4 by the reference arrow 76. While engaged in this manipulation of the support rod 50 it will of course be understood that the surgeon continues to sight down the laparoscope 10, so that he can determine when the laparoscope proximal end 10b is in the precise anatomy-viewing position which he requires.

Still referring to FIG. 4, it will be understood and appreciated that the physical relationship of the components which comprises the present invention is such that the conical traverse 76 of the support rod 50 provides a corresponding conical traverse in the laparoscope 10, said traverse being designated 76a in FIG. 4, and, even more important, that there also results a corresponding conical traverse in the laparoscope proximal end 10b, but of a significantly diminished extent, designated 76b in FIG. 4. In this regard and still referring to FIG. 4, it will be noted that the mechanical relationship between the location of the ball and socket joint 40 and the incision 74 in the patient for the laparoscope proximal end 10b are approximately in the same plane, which in FIG. 4 is signified by the reference line 78, such that there is the relationship between the movements 76 and 76b, as just noted. This is important since with experience the surgeon can achieve proper anatomy-viewing positioning for the laparoscope proximal end 10b with deft manipulation of the upper end of the support rod 50. Stated another way, it can be readily appreciated that there is a corresponding relationship in the movements 76a and 76 of the respective upper ends of the laparoscope 10 and support rod 50, and that therefore likening the exposed length portion of the laparoscope 10 to a lever with a fulcrum located at the incision 74, it will be readily appreciated that angular movement of the upper end 10a in a conical movement 76a will result in an equal annular or conical movement of the laparoscope proximal end 10b, but at a diminished extent because of the difference in distances from the fulcrum 74 of these two opposite ends.

It also should be noted and recognized as a significant contribution of the present invention that during the time that the laparoscope 10 is being positioned as just described, that the weight thereof, as well as the weight of the connecting member 60, as well as that of the support rod 50 itself, is effectively supported in the seat or socket compartment of the sleeve 44 inasmuch as the sleeve is in supporting relation beneath the ball 48 of the ball and socket joint 40, all as is clearly illustrated in FIG. 2. Since the components just described are in turn effectively supported on the fixed open ring 18, there is thus no possibility that due to the weight of the components, even during the pivotal traverses 76 of the laparoscope proximal end 10b, that said end of the laparoscope will exert pressure on tissues, and especially on soft organs, such as the liver, pancreas, intestines, etc., which, of course, it is important to avoid.

Once the laparoscope proximal end 10b is in the precise viewing position required by the surgeon and fixed in said position, the surgical procedure then contemplates the making of an additional incision 80 in the approximate location of the laparoscope to be used by the surgeon in achieving the surgical objective or result. It will of course be understood that the size of the incision 80 is characterized by being of a nominal extent because the surgeon is not required to use the incision opening 80 to view the internal anatomy, since this is the function of the laparoscope 10.

For completeness sake, it is noted that the laparoscope 10 is equipped with a conventional light source attachment 82 and also an attachment 84 to a source of carbon dioxide, which, in a well understood manner, is used during surgery to separate the abdominal contents and also reduce the risk of puncturing a bowel.

In addition to the surgeon sighting through the laparoscope 10, it is also a known practice, and therefore illustrated in phantom perspective in FIG. 1, to mount a television camera 86 in viewing relation to the laparoscope eyepiece 10c and to operatively connect the camera 86 via the electrical connector 88 to a TV monitor 90 having a display screen 92. In this manner, a number of surgeons can attend the patient P during the surgical procedure and can offer assistance based on observation of the images transmitted and displayed on the screen 92. A TV camera 86 which is under the weight limit which could inadvertently produce movement in the rigidified member 60 is readily available from numerous commercial sources, one such source being model S2-2 from Codman Instruments of Randolph, Mass.

Although the surgical procedure described herein is in the category of general surgery, it will be understood that the holder and positioner for the laparoscope is equally applicable for orthopedics, pediatric surgery, urology, gynecology, thoracic surgery, heart and vascular surgery, neurosurger animal surgery and veterinary surgery. Also, the holding and positioning components described herein are preferred for use with a laparoscope, but are equally applicable for use with an endoscopic system.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. For surgical manipulation of a laparoscope engaged adjacent its exposed distal end and requiring its inserted proximal end to be positioned in proper viewing relation to anatomy to be observed therethrough, an assembly comprising, in combination, an open ring and means for supporting same in a fixed horizontal orientation over a patient having an incision for the insertion of said laparoscope proximal end, a generally vertically oriented support rod mounted adjacent its lower end at a selected location on said open ring, a selectively tensionable member extending from an end thereof engaged to said laparoscope to engagement of its opposite end to the upper end of said support rod such that prior to the tensioning of said tensionable member said laparoscope proximal end is manipulatable into a position that is proximate to that for proper viewing of said anatomy, and a ball and socket joint at said lower end of said support rod for permitting said rod to be urged through conical movement, whereby said laparoscope proximal end partakes of corresponding conical movement incident to assuming a more precise anatomy-viewing position while the weight of said assembly and laparoscope remains supported on said open ring.

2. The assembly for holding and positioning a laparoscope as claimed in claim 1 wherein said tensionable member is comprised of interconnected link elements each having a ball-shape at one end and a complementary ball socket at its other end, and is of the type effective to assume a wide range of selected rigid shapes so as to contribute to providing said anatomy-viewing position of said laparoscope.

3. The assembly for holding and positioning a laparoscope as claimed in claim 2 including a TV camera operatively disposed on said laparoscope for viewing therethrough, and a TV monitor electronically connected to said TV camera to display images as seen through said laparoscope.

4. For surgical manipulation of a laparoscope engaged adjacent it exposed distal end and requiring its inserted proximal end to be positioned in proper viewing relation to anatomy to be observed therethrough, an assembly comprising, in combination, an operating table support operatively disposed to extend over a patient having an incision for the insertion of said laparoscope proximal end, a generally vertically oriented support rod mounting adjacent its lower end on said operating table support, a selectively tensionable interconnected operative arrangement of link elements extending from an end thereof engaged to said laparoscope to engagement of its opposite end to the upper end of said support rod such that prior to the tensioning of said interconnected link elements into a rigid shape said laparoscope proximal end is manipulatable into a position that is proximate to that for proper viewing of said anatomy, and a ball and socket joint at said lower end of said support rod for permitting said rod to be urged through conical movement, whereby said laparoscope proximal end partakes of corresponding conical movement incident to assuming a more precise anatomy-viewing position while the weight of said assembly and laparoscope remains supported on said operating table support.

* * * * *